United States Patent
Koh et al.

(10) Patent No.: US 7,091,016 B2
(45) Date of Patent: Aug. 15, 2006

(54) **CARBONYL REDUCTASE OF *KLUYVEROMYCES MARXIANUS* AND ITS ISOLATION AND PURIFICATION METHOD**

(75) Inventors: Hun-Yeong Koh, Kyonggi-Do (KR); Ye-Sun Han, Seoul (KR); Joo-Hwan Cha, Seoul (KR); Wook-Hyun Kim, Seoul (KR); Jong-Soo Lee, Kyonggi-Do (KR); Hong-Chul Yun, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 467 days.

(21) Appl. No.: 10/346,831

(22) Filed: Jan. 17, 2003

(65) Prior Publication Data

US 2003/0170844 A1 Sep. 11, 2003

(30) Foreign Application Priority Data

Jan. 26, 2002 (KR) ............... 10-2002-0004657

(51) Int. Cl.
*C12N 9/02* (2006.01)
(52) U.S. Cl. .................. 435/189; 435/255.1
(58) Field of Classification Search ............. 435/189
See application file for complete search history.

(56) References Cited

U.S. PATENT DOCUMENTS

2003/0175886 A1* 9/2003 Han et al. ............... 435/69.1

FOREIGN PATENT DOCUMENTS

EP 0 290 385 B1 11/1988

OTHER PUBLICATIONS

Online Korean Catalogue 2003 No. 1930 p. 4 Strain 7155 *Kluyveromyces marxianus*.*
Wermuth, Bendicht, "Enzymology of Carbonyl Metabolism 2: Aldehyde Dehydrogenase, Aldo-Keto Reductase, and Alcohol Dehydrogenase", Biol. Res., 1985, vol. 174, pp. 209-230.
Oppermann, Udo C.T., et al., "Molecular and structural aspects of xenobiotic carbonyl metabolizing enzymes. Role of reductases and dehydrogenases in xenobiotic phase I reactions", Toxicology, 2000, vol. 144, pp. 71-81.

* cited by examiner

*Primary Examiner*—Herbert J. Lilling
(74) *Attorney, Agent, or Firm*—Darby & Darby

(57) ABSTRACT

Carbonyl reductase (CR) of a yeast strain, *Kluyveromyces marxianus*, and its isolation and purification method thereof is provided. The reduction reaction by the reductase obtained in the present invention is more stereospecific and requires less cost and time than the reduction reactions by the microorganisms or by the reducing enzymes obtained from a chemical synthesis.

4 Claims, 4 Drawing Sheets

Reaction of Carbonyl Reductase

SEQUENCE LISTING

<160> NUMBER OF SEQ ID NOS: 1

<210> SEQ ID NO 1
<211> LENGTH: 7
<212> TYPE: PRT

```
-continued

<213> ORGANISM: Kluyveromyces marxianus

<400> SEQUENCE: 1

Thr Phe Thr Val Val Thr Gly
1               5
```

CARBONYL REDUCTASE OF *KLUYVEROMYCES MARXIANUS* AND ITS ISOLATION AND PURIFICATION METHOD

TECHNICAL FIELD

The present invention relates to carbonyl reductase of a yeast strain, *Kluyveromyces marxianus* and its isolation and purification method.

BACKGROUND OF THE INVENTION

In general, carbonyl compounds exhibit in vivo toxicity due to their high reactivity. Carbonyl reductase is known to detoxify such carbonyl compounds by reducing them [Udo C. T. Oppermann, Toxicology 144 (2000) 71–81]. Carbonyl reductase usually exists as monomers and has diverse substrate specificities to different carbonyl compounds [B. Wermuth, Clin. Biol. Res. 174 (1985) 209–230].

Generally, the methods of reducing the above carbonyl compounds includes those using the microorganisms that have the reducing enzymes or using the reducing enzymes obtained from a chemical synthesis.

Asymmetric reduction of carbonyl compounds by using microorganisms such as yeast is a very useful method to synthesize optically active chemical compounds. The conventional reduction of carbonyl compounds by using microorganisms, however, yield (S)-alcohols preferably to (R)-alcohols. Asymmetric mixture of (2S,3R) and (2R,3R) compounds is produced when α-substituted β-keto esters are reduced. The ratio between the two products depends greatly on the substituting group at the α position. Generally, yeast is known to produce (S)-3-hydroxy compounds by reducing β-keto esters (European patent 0290385), and carbonyl reductases of yeast, known up to date, produce asymmetric mixture of (2S,3R) and (2R,3R) compounds.

Even though it is convenient and economical to carry out the reduction reaction by the above method using microorganisms, it is difficult to obtain compounds that are highly stereospecific to substrates since many oxidases and reductases exist in reality. Chemical synthesis of reductase requires complex production process, time and cost since many steps must be carried out for the reaction. Therefore, there is a demand for easy and economical methods for obtaining the carbonyl reductase that is highly stereospecific to substrates.

To overcome the above problems, the present invention provides highly stereoselective carbonyl reductase that can be purified and synthesized easily by separating an enzyme that reduces carbonyl compounds from a yeast strain, *Kluyveromyces marxianus*, by identifying the amino-terminal sequence and by purifying the reductase.

DETAILED DESCRIPTION OF THE INVENTION

The present invention relates to a carbonyl reductase (CR) of a yeast strain, *Kluyveromyces marxianus*, and an isolation and purification method thereof. The present invention also provides the amino-terminal sequence by identifying the amino acid sequence of the above reductase.

As shown in FIG. 1, the method of separating and purifying a carbonyl reductase according to the present invention includes the steps of (1) cultivating *Kluyveromyces marxianus*;
(2) collecting the cultivated cells from the culture medium by centrifugation and then lysing the cells; and
(3) collecting the supernatant after centrifuging the above cell lysate, and separating and purifying the active material against the substrates by subjecting the obtained supernatant to column chromatography.

The above *Kluyveromyces marxianus* can be cultivated at 28~32° C. until the optical density (O.D) reaches about 7.0 at 600 nm ($OD_{600}$=about 7.0). The media conventionally used in the cultivating process, including YM medium, can be used. The centrifugation process in the above step (2) is carried out at 2800~3200 g. There is no restriction in the way for lysing or crushing cells. After carrying out the centrifugation process in the above step (3) at 2400~2600 g, the supernatant is obtained for column chromatography. In each step of the column chromatography, the enzyme activity against the substrate is measured by HPLC. The fractions exhibiting the enzyme activity is separated and purified. Q sepharose, phenyl sepharose, HiTrap Blue and gel filtration chromatography columns can be used sequentially to separate the carbonyl reductase.

The size of the above protein is approximately 40~42 kDa (FIG. 2) as analyzed by running 12% SDS-polyacrylamide gel. The active temperature and pH ranges were determined by measuring the activity of the enzyme against the substrate. The active temperature is 25~35° C., and preferably 30° C. The active pH is 6.5~7.5, and preferably 6.8. The activity of the above protein at 30° C. and pH 6.8 is shown in FIG. 4.

As shown in FIG. 3, *Kluyveromyces marxianus* produces 4 different isomers, (2S,3R), (2R,3S), (2R,3R) and (2S,3S) by reducing the substrate. On the other hand, carbonyl reductase purified according to the present invention from *Kluyveromyces marxianus* produces asymmetric isomers, (2S,3R) and (2R,3R) by reacting with the substrate, as shown in FIG. 4. It is distinctly different from the known enzymatic reaction of the yeast reductase which produces two asymmetric compounds, (2R,3S) and (2S,3S).

Also, the amount of the obtained protein in each column step and the carbonyl reductase activity of the protein are listed in Table 1. The amount of the obtained protein in each column step was determined by Bradford analysis method [Bradford, M., Anal. Biochem., (1976) 72–248].

TABLE 1

| step | Total protein (mg) | Total activity (units) | Specific activity (units/mg) | Recovery (%) | Purification (-fold) |
|---|---|---|---|---|---|
| Supernatant of cell lysate | 6,051.54 | 185.92 | 0.0307 | 100 | 1 |
| Q sepharose | 496.83 | 56.74 | 0.1142 | 30.52 | 3.72 |
| Phenyl sepharose | 59.49 | 32.08 | 0.5392 | 17.25 | 17.56 |
| Hi trap Blue | 14.29 | 12.59 | 0.8810 | 6.77 | 28.70 |
| Gel filtration chromatography | 4.36 | 6.43 | 1.4748 | 3.46 | 48.04 |

The amino-terminal sequence of the separated and purified protein was determined by adsorbing it on a PVDF membrane.

EXAMPLE 1

Separation and Purification of Reductase from *Kluyveromyces marxianus*

*Kluyveromyces marxianus* (KCTC accession No. 7155) was cultivated in 8 L YM medium at 30° C. for 3 days until OD becomes approximately 7.0 at 600 nm. The medium was prepared by mixing 970 ml of distilled water and YM Broth [0.3% (w/v) Bacto Yeast Extract, 0.3% (w/v) Malt Extract, 0.5% (w/v) Bacto Peptone, 1% (w/v) Bacto Dextrose] quantity sufficient to make 1L and by sterilizing. The *Kluyveromyces marxianus* was cultivated in 10 ml in the beginning and inoculated in 1 L of the medium at 30° C. for 48 days with shaking until OD becomes approximately 7.0 at 600 nm. Approximately 8 L was obtained from one time cultivation. The cultured cells were centrifuged at 3000 g for 10 min and then collected. The obtained cells were dissolved in 500 ml of the dilution buffer solution (20 mM Tris-HCl, pH 8.0), and then eliminated the remaining medium by centrifugation. Phenylmethylsulfonyl fluoride (PMSF, Sigma) solution at 1 mM was added in the dilution buffer. The cells were crushed in the French Pressure Cell Press working at 11,000 bar. The cells were further crushed by sonicating (in Branson sonifier, Model 450) 5 times for 5 min each. The obtained cell lysate was centrifuged for 30 min at 25,000 g. After separating the supernatant by using anion exchange chromatography (Q sepharose, FPLC, LKB Pharmacia), the activity against ethyl 2-phthalimidoylm-ethyl-3-oxobutanoate was measured for each eluent by HPLC (Waters) (FIGS. 2 and 3).

After collecting the solutions exhibiting the activity together, ammonium sulfate (AMS) was added to the solution so as to make the final concentration of AMS to become 1.0 M. Subsequently, the solution was separated through phenyl sepharose column (Amersham Pharmacia Biotech). The eluents exhibiting the activity were separated by using the affinity column, Hi trap blue (Amersham Pharmacia Biotech) and finally by gel filtration chromatography (Superdex-75, FPLC, LKB Pharmacia).

Figure 1:
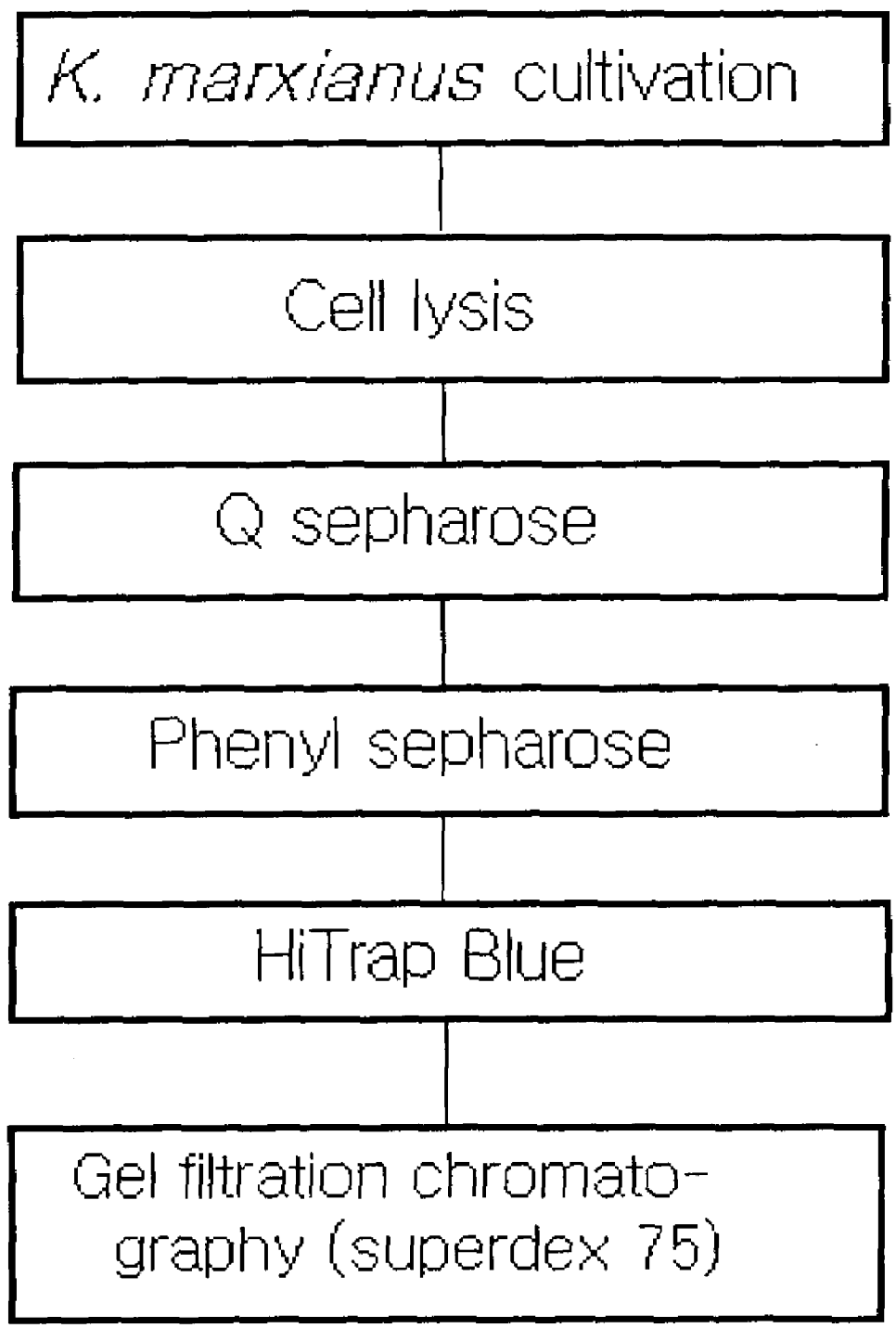
FIG. 1 is an overall schematic describing the procedure for separating carbonyl reductase of the present invention.
Figure 2:
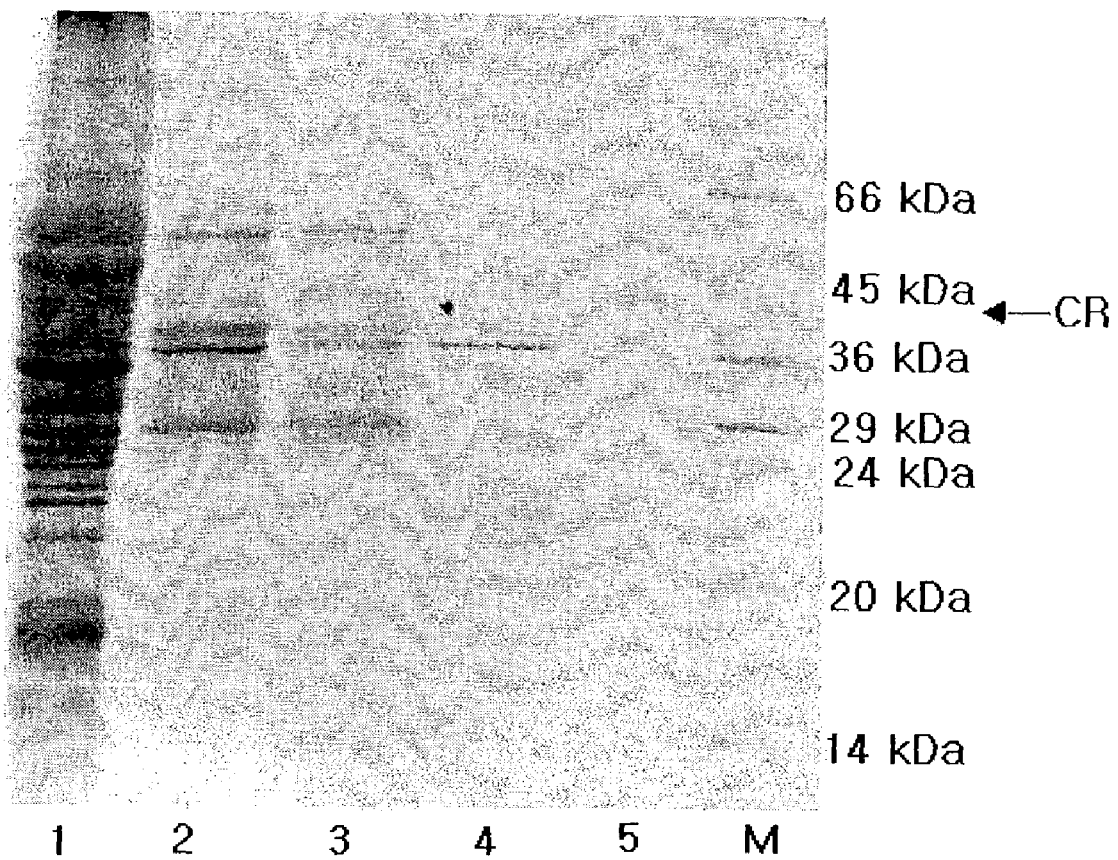
FIG. 2 is a result of SDS-polyacrylamide gel (12%) electrophoresis to determine the purity of the carbonyl reductase. Column M shows a standard molecular weight marker, column 1 shows the supernatant of cell lysate, columns 2, 3, 4 and 5 show the results of Q sepharose, phenyl sepharose, Hi trap Blue and gel filtration chromatography, respectively.
Figure 3:
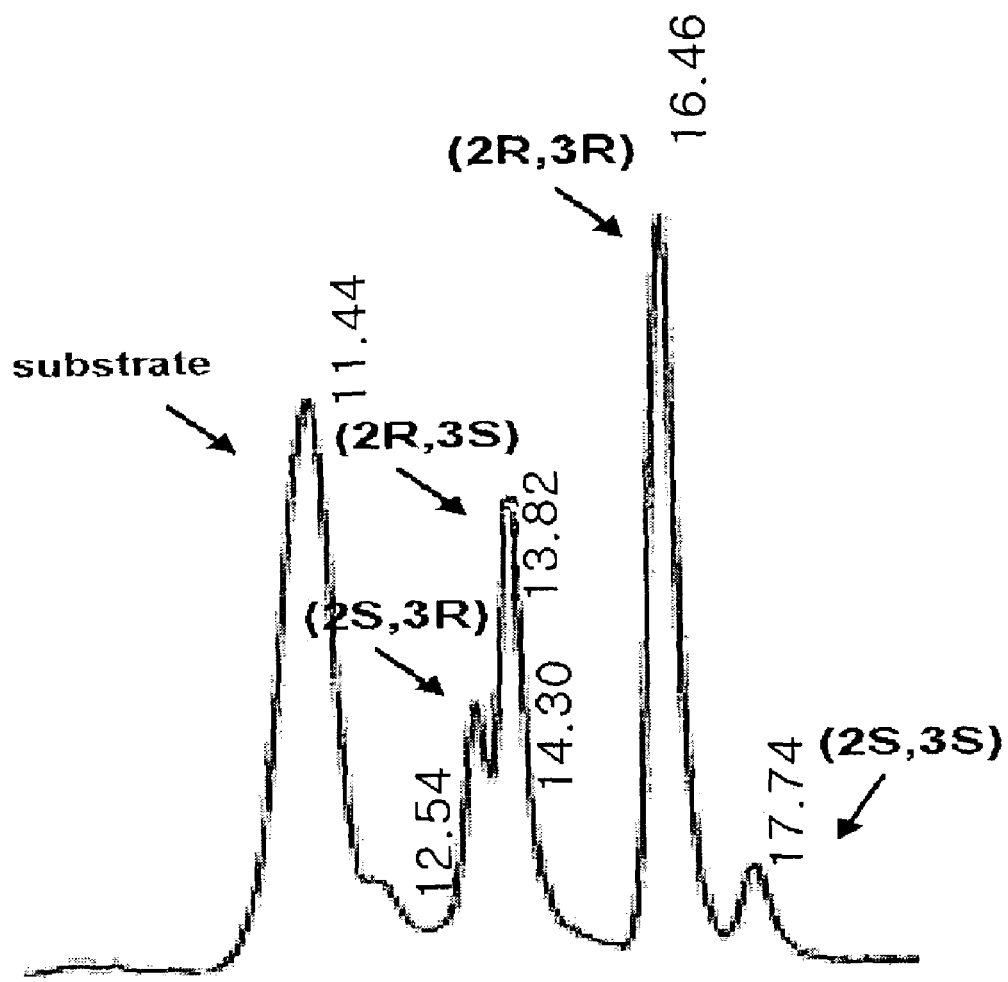
FIG. 3 shows a process of determining the activity of *Kluyveromyces marxianus* by performing HPLC.
Figure 4:
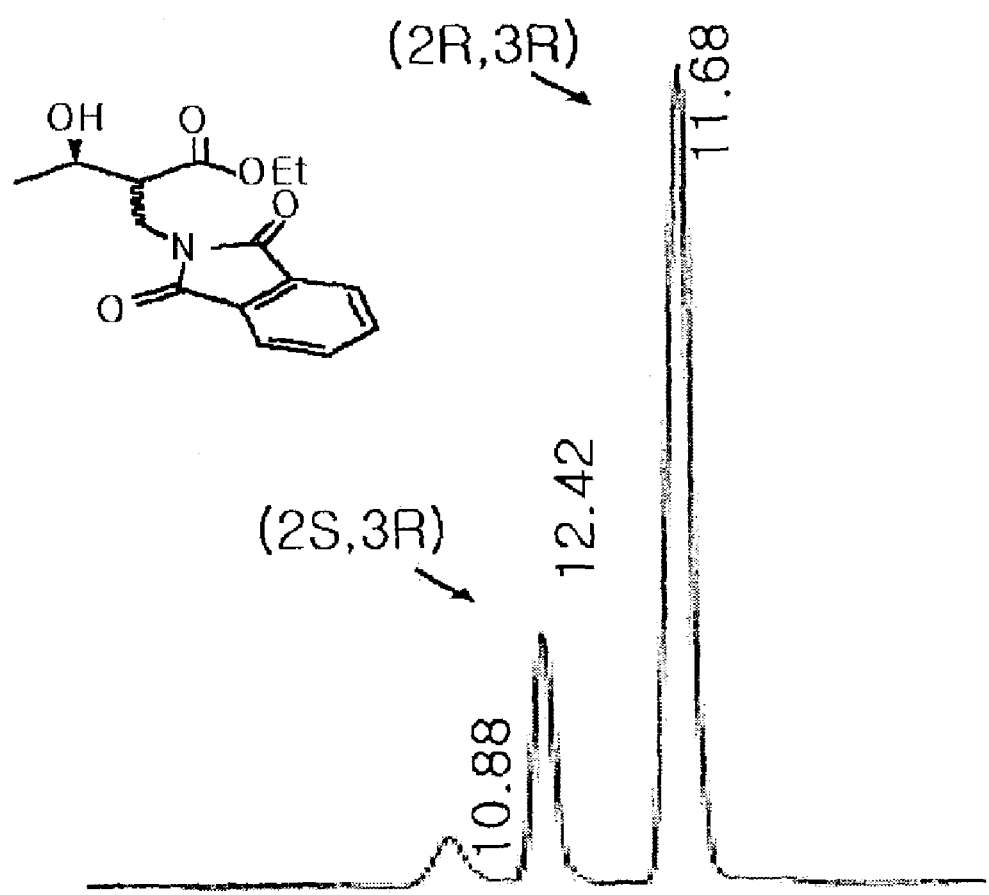
FIG. 4 shows the process of determining the optimum activity of the carbonyl reductase purified according to the present invention at the reaction temperature of 30° C. and reaction pH of 6.8 by performing HPLC.

Purified protein was confirmed by identifying a protein band corresponding to the molecular weight of approximately 40 kDa by 12% SDS-polyacrylamide gel electrophoresis (FIG. 2). The amount of protein obtained from each step of the column separation was measured by Bradford method. The amino-terminal sequence of the protein was obtained by identifying the sequence after transferring the protein on a PVDF membrane. The amino-terminal sequence was obtained by Edman degradation method. The analysis was carried out by Korea Basic Science Institute.

Amino-terminal sequence $^1$Thr-Phe-Thr-Val-Val-Thr-$^7$Gly (SEQ ID NO: 1)

EXAMPLE 2

Reaction of *Kluyveromyces marxianus* Reductase

Ten micro-liters of β-NADPH solution (1.14 mg in sodium phosphate buffer solution, 2.0 eq) was suspended in 190 ml of sodium phosphate buffer solution (100 mM, pH 6.8, Sigma). After adding 50 μl of the enzyme solution and 12.5 μl of ethyl 2-(1,3-dioxo-1,3-dihydro-isoindol-2-ylm-ethyl)-3-oxo-butyrate (10 mg in 0.5 ml ethanol), the suspension was reacted in a stirring incubator in which the temperature was adjusted to 30° C. After the reaction, 100 μl of this solution was taken out and the organic phase was extracted with the same amount of ethyl acetate therefrom. Fifty micro-liters of the organic phase was collected, diluted by adding 1 ml of the mobile phase (hexane:isopropyl alcohol=93:7, v/v), and then, analyzed by HPLC. The following asymmetric reduction products were produced as a result of the above reduction reaction. Since the asymmetric reduction products have optical activities, the reductase according to the present invention is useful in synthesizing optically active drug intermediates for producing drugs.

(2S,3R) ethyl 2-(1,3-dioxo-1,3-dihydro-isoindol-2-ylm-ethyl)-3-hydroxy-butyrate $^1$H NMR (CDCl$_3$, 300MHz) δ 7.73 (m, 4H, ph), 4.00 (m, 5H, CHCH$_2$Npht, —CHOH, —OCH$_2$CH$_3$), 2.62 (m, 1H, —CHCH$_2$), 1.19 (d, 3H, J=6.1 Hz, —CH$_3$CH) 1.12 (t, 3H, J=7.1 Hz, —OCH$_2$CH$_3$).

(2R,3R) ethyl 2-(1,3-dioxo-1,3-dihydro-isoindol-2-ylm-ethyl)-3-hydroxy-butyrate $^1$H NMR (CDCl$_3$, 300MHz) δ 7.73 (m, 4H, ph), 3.98 (m, 5H, CHCH$_2$Npht, —CHOH, —OCH$_2$CH$_3$), 2.76 (m, 1H, —CHCH$_2$), 1.26 (d, 3H, J=6.5 Hz, —CH$_3$CH) 1.10 (t, 3H, J=7.1 Hz, —OCH$_2$CH$_3$)

In the present invention, an enzyme that reduces carbonyl compounds was separated from a yeast strain, *Kluyveromyces marxianus*, and the amino-terminal sequence was identified. The present invention provides highly stereoselective carbonyl reductase that can be purified and synthesized easily by a simple procedure. The amino acid sequence of the above carbonyl reductase of *Kluyveromyces marxianus* will provide a fundamental information for the expression of this enzyme. Moreover, the reductase can be used in synthesizing optically active drug intermediates to produce stereoselectively pure compounds. Also the enzyme can be expressed in a large quantity in *E. coli* to synthesize intermediates of biologically active compounds.

The invention claimed is:

1. A carbonyl reductase, separated from *Kluyveromyces marxianus* and purified, having 40~42 kDa in size and active at the temperature range of 25~35° C. and the pH range of 6.5~7.5.

2. The carbonyl reductase according to claim 1, having $^1$Thr-Phe-Thr-Val-Val-Thr-$^7$Gly sequence at the amino terminus.

3. A method of obtaining the carbonyl reductase of claim 1 from *Kluyveromyces marxiamus* including the steps of (1) cultivating *Kluyveromyces marxianus*,
(2) collecting the cultivated cells from the culture medium by centrifugation and then, lysing the cells, and
(3) collecting the supernatant after centrifuging the above cell lysate, and separating and purifying the active material against the substrates by subjecting the obtained supernatant to column chromatography.

4. The method according to claim 3, comprising the steps of sequentially using Q sepharose, phenyl sepharose, HiTrap Blue and gel filtration chromatography.

* * * * *